(12) United States Patent
McRury et al.

(10) Patent No.: US 7,582,097 B2
(45) Date of Patent: Sep. 1, 2009

(54) SUTURE WELDING SYSTEM AND METHOD

(75) Inventors: Ian D. McRury, Medway, MA (US);
Douglas W. Dunn, Mansfield, MA (US);
Nathan S. Cauldwell, Mansfield, MA (US)

(73) Assignee: Ethicon, Inc., Somerville, NJ (US)

( * ) Notice: Subject to any disclaimer, the term of this patent is extended or adjusted under 35 U.S.C. 154(b) by 247 days.

(21) Appl. No.: 10/024,625

(22) Filed: Dec. 18, 2001

(65) Prior Publication Data
US 2003/0114864 A1 Jun. 19, 2003

(51) Int. Cl.
*A61B 17/04* (2006.01)
(52) U.S. Cl. .................. 606/148; 606/139; 606/144
(58) Field of Classification Search .................. 606/32, 606/33, 48–52, 148, 139, 144
See application file for complete search history.

(56) References Cited

U.S. PATENT DOCUMENTS

| | | | |
|---|---|---|---|
| 3,657,056 A | | 4/1972 | Winston et al. |
| 3,702,948 A | * | 11/1972 | Balamuth .............. 310/323.18 |
| 4,052,988 A | * | 10/1977 | Doddi et al. ................ 606/231 |
| 4,662,068 A | * | 5/1987 | Polonsky ..................... 30/124 |
| 5,258,006 A | * | 11/1993 | Rydell et al. ................ 606/205 |
| 5,269,809 A | | 12/1993 | Hayhurst et al. |
| 5,336,221 A | * | 8/1994 | Anderson ..................... 606/27 |
| 5,342,359 A | * | 8/1994 | Rydell .......................... 606/51 |
| 5,383,883 A | | 1/1995 | Wilk et al. |
| 5,417,700 A | | 5/1995 | Egan |
| 5,565,122 A | | 10/1996 | Zinnbauer et al. |
| 5,893,880 A | * | 4/1999 | Egan et al. ................... 606/228 |
| 6,010,516 A | * | 1/2000 | Hulka ......................... 606/148 |
| 6,077,277 A | | 6/2000 | Mollenauer et al. |
| 6,106,545 A | | 8/2000 | Egan |
| 6,165,183 A | | 12/2000 | Kuchn et al. |
| 6,174,324 B1 | | 1/2001 | Egan et al. |
| 6,277,117 B1 | * | 8/2001 | Tetzlaff et al. ................ 606/48 |
| 6,358,271 B1 | * | 3/2002 | Egan et al. ................... 606/228 |
| 6,409,743 B1 | * | 6/2002 | Fenton, Jr. ................... 606/232 |

(Continued)

FOREIGN PATENT DOCUMENTS

JP 11-56859 3/1999

(Continued)

OTHER PUBLICATIONS

JP Office Action dated Jan. 13, 2009, from corresponding JP Appl No. 2002-365673, w/English translation.

*Primary Examiner*—Darwin P Erezo (57) ABSTRACT

A suture welding system for fixedly attaching a first length of suture to a second length of suture includes an electrosurgical energy source and a suture welding device. The suture welding device has a working end, a suture contacting element disposed on the working end, a first electrode electrically coupled to the electrosurgical energy source, and a second electrode electrically coupled to the electrosurgical energy source. The first electrode is disposed on the suture contacting element for providing electrical energy to the first and second lengths of suture, and the second electrode is disposable proximate to the suture welding site for providing a return electrical energy path to the electrosurgical energy source. When electrical energy is provided by the first electrode to the first and second lengths of suture welds, the first and second lengths of suture are welded into a fixed attachment.

21 Claims, 5 Drawing Sheets

U.S. PATENT DOCUMENTS

| | | | |
|---|---|---|---|
| 6,423,088 B1 * | 7/2002 | Fenton, Jr. | 606/232 |
| 6,464,704 B2 * | 10/2002 | Schmaltz et al. | 606/51 |
| 6,488,690 B1 * | 12/2002 | Morris et al. | 606/144 |
| 6,669,705 B2 * | 12/2003 | Westhaver et al. | 606/139 |
| 2002/0173821 A1 * | 11/2002 | Fenton et al. | 606/228 |

FOREIGN PATENT DOCUMENTS

| | | |
|---|---|---|
| WO | WO 99/26542 | 6/1999 |
| WO | WO 01/87165 | 11/2001 |

* cited by examiner

SUTURE WELDING SYSTEM AND METHOD

FIELD OF THE INVENTION

The present invention relates to systems, devices and methods for welding lengths of suture to create a fixed attachment between lengths of suture without tying knots.

BACKGROUND OF THE INVENTION

Many surgical procedures include the use of sutures, particularly for tissue fixation and repair, and often in endoscopic, arthroscopic or other minimally invasive procedures for effecting surgical procedures within a patient's body. Traditionally, once a suture is appropriately positioned with respect to the relevant tissue, the suture ends are knotted together to fix or otherwise repair the tissue. These suture knots may either be formed proximate to the fixation or repair site, or away from the surgical site and outside of the A surgical field. In the latter situation, so-called "knot pusher" devices and methods have been developed to transport the knotted region of the suture to the tissue or to another desired location. In either situation, knots may be difficult to make, difficult to properly tension and difficult to properly place, particularly in tight spaces.

Suture fixation techniques other than knotting have also been tried. For example, techniques and apparatus for performing frictional suture welding have been disclosed. Such frictional welding is generally accomplished by exposing the suture fixturing and/or directly exposing the suture material to ultrasonic energy. U.S. Pat. No. 3,515,848 to Winston et al. discloses devices and methods for ultrasonic suture welding. More recently, patents assigned to Axya Medical, Inc. of Beverly, Mass. (see, e.g., U.S. Pat. Nos. 5,417,700; 5,893,880; 6,174,324) have disclosed devices and methods involving the application of ultrasonic energy to weld sutures. This method, however, does not work with all popular suture materials, and proper welding can be sensitive to suture placement and configuration within the welding device.

Accordingly, there remains a need to fix sutures without the need to tie knots. In particular, it would be desirable to develop a system to weld lengths of popular suture materials, such as polydioxanone (PDS), to fix one length of suture to another without the need for knots. It would further be desirable to develop techniques for fixing sutures that use an energy source that is already commonplace in the surgical venue, thus eliminating the need for significant new capital investment.

SUMMARY OF THE INVENTION

The present invention solves the described problems in the art and others by providing a suture welding system for fixedly attaching a first length of suture to a second length of suture. A suture welding system of the invention includes an electrosurgical energy source and a suture welding device. The suture welding device has a working end, a suture contacting element disposed on the working end, a first electrode electrically coupled to the electrosurgical energy source, and a second electrode electrically coupled to the electrosurgical energy source. The first electrode is disposed on the suture contacting element for providing electrical energy to the first and second lengths of suture, and the second electrode is disposable proximate to the suture welding site for providing a return electrical energy path to the electrosurgical energy source. When electrical energy is provided by the first electrode to the first and second lengths of suture, the first and second lengths of suture are welded into a fixed attachment.

In a further aspect of the invention, the suture welding device includes a proximal handle, a distal end, and a suture grasper disposed on the distal end for holding first and second lengths of suture. The suture grasper has first and second suture grasping members with at least one suture grasping member being moveable with respect to the other suture grasping member. An actuator is disposed on the proximal handle and coupled to the suture grasper for selectively moving the suture grasper between a first, open grasper position and a second, closed grasper position. In the open position, the first and second suture grasping members are spaced apart to allow first and second lengths of suture to be placed within the suture grasper. In the closed position, the first and second suture grasping members are spaced so as to hold the first and second lengths of suture thread within the suture grasper. First and second electrodes are electrically coupled to the electrosurgical energy source and disposed on the suture grasper for providing electrical energy to the first and second lengths of suture thread. As with the previously described aspect of the invention, the provision of electrical energy by the electrodes to the first and second lengths of suture welds the first and second lengths of suture into a fixed attachment.

In either aspect of the invention, the electrosurgical energy source can preferably provide energy in the form radio frequency waves, and the radio frequency waves provided can have a frequency of between about 100 KHz and 1 MHz.

Relative movement between suture grasping members can come about by having one suture grasping member slidingly engaged with the other suture grasping member to result in relative movement essentially along a longitudinal axis of the suture welding device to open and close the suture grasper. Alternatively, one suture grasping member can pivotally engage the other suture grasping member so that a gap between the suture grasping members decreases in a direction substantially orthogonal to a longitudinal axis defined by the suture welding device when the suture grasper is selectively moved from the first, open grasper position to the second, closed grasper position. The suture welding device can also include a piston slidingly engaged with the suture welding device so as to be translatable in a longitudinal direction to encourage contact between the first and second lengths of suture and at least one electrode.

A weldable material can also be provided between at least one electrode and at least one length of suture. The weldable material provided can weld the first length of suture thread to the second length of suture thread upon application of electrical energy through the at least one electrode. This embodiment can be particularly useful when working with suture material that is not itself weldable.

In a preferred embodiment, the first and second lengths of suture can be made of material selected from polydioxanone, prolene, and polymer plastics. In a further preferred embodiment, the first and second lengths of suture can be made of polydioxanone (PDS).

In a further embodiment, the suture welding device includes a temperature sensor disposed proximate to at least one electrode, and the electrosurgical energy source communicate with the temperature sensor and stops the delivery of energy based on the temperature sensed. Still further, the electrosurgical energy source can include a timer and stop the delivery of energy to the electrodes after the energy has been supplied for a predetermined amount of time when welding is complete.

A method of the invention for welding a first length of suture to a second length of suture to create a fixed attachment therebetween starts with the provision of an electrosurgical energy source and a suture welding device. The suture welding device includes a working end, a suture contacting element disposed on the working end, a first electrode electrically coupled to the electrosurgical energy source and disposed on the suture contacting element for providing electrical energy to the first and second lengths of suture, and a second electrode electrically coupled to the electrosurgical energy source and disposable proximate to the suture welding site for providing a return electrical energy path to the electrosurgical energy source. The first and second lengths of suture are placed into contact with the suture contacting element and electrical energy from the electrosurgical energy source is provided through the first electrode to the first and second lengths of suture to weld the first length of suture to the second length of suture to create a fixed attachment therebetween.

BRIEF DESCRIPTION OF THE DRAWINGS

The invention will be more fully understood from the following detailed description taken in conjunction with the accompanying drawings.

DETAILED DESCRIPTION OF THE INVENTION

The present invention provides systems and methods useful for welding a first length of suture to a second length of suture to create a fixed attachment between the two lengths of suture. In general, a suture welding device having a suture contacting element with at least one electrode located thereon is coupled to an energy source so that energy can be delivered to first and second lengths of suture in a manner that allows the lengths of suture to be welded to each other.

Figure 1:
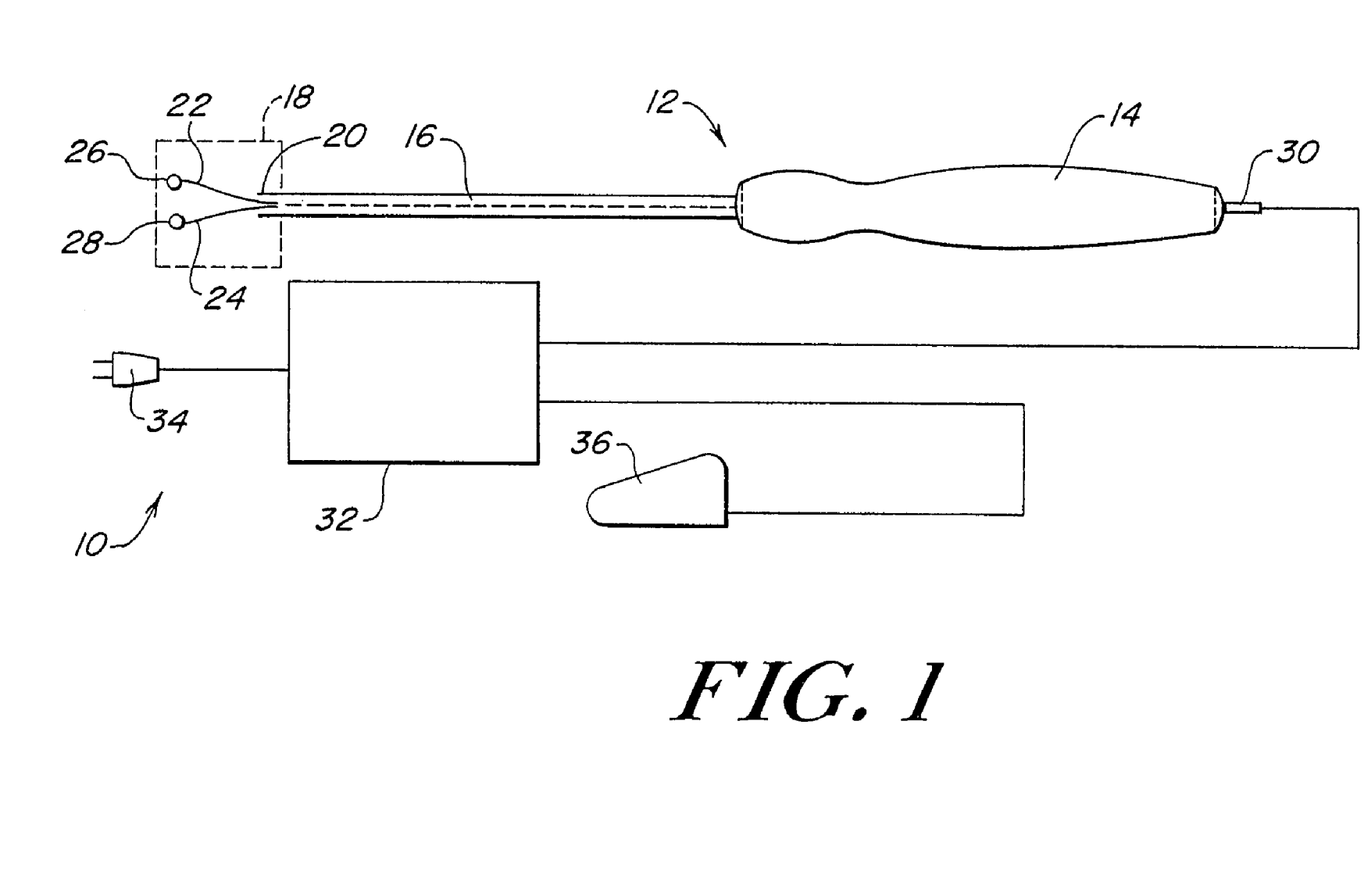
FIG. 1 is a schematic representation of a suture welding system of the invention.

A schematic representation of a suture welding system 10 of the invention is shown in FIG. 1. System 10 includes an energy source 32 and a suture welding device 12. Suture welding device 12 includes a proximal handle 14 that may be gripped by a surgeon, and a distal extender tube 16 having a suture grasper or suture contacting element 18 on its distal or working end 20. As illustrated, suture contacting element 18 includes first and second suture grasping members 22, 24 and has first and second electrodes 26, 28 disposed on the first and second grasping members, respectively. Electrodes 26, 28 are electrically coupled to energy source 32 by a connector and cable connected at the proximal end 30 of suture welding device 12. As illustrated, suture grasping element 18 has two grasping members 22, 24, however, a person of ordinary skill in the art will recognize that more or fewer elements could be used to couple electrical energy from energy source 32 to lengths of suture that are to be fixedly attached. In addition, the illustrated embodiment presupposes bipolar delivery of energy through two electrodes 26, 28; a person of ordinary skill in the art will recognize that the energy could also be supplied in a monopolar fashion using a single electrode on the suture contacting element and a return electrode disposed on a patient proximate to a suture welding site (proximate in the sense that the return electrode is capable of performing its desired function from that location).

An electrical energy source 32 is electrically coupled to suture welding device 12. Energy source 32 can be conventionally powered by connecting to a standard AC electrical source by plug 34, and can include a foot pedal 36 or other actuator. Energy source 32 can be one of a variety of electrosurgical energy sources that are typically found in a hospital or out-patient care setting. In a preferred embodiment, energy source 32 is a radio frequency or RF energy source. As used herein, the term radio frequency refers to frequencies that are higher than those used in cutting/coagulating applications, and are preferably between about 100 KHz and 1 MHz, and more preferably between about 300 KHz and 500 KHz.

Energy source 32 can also preferably include an appropriate controller for shutting off energy to electrodes 26, 28 upon completion of welding. In general, welding occurs based on Ohmic heating of resistive material through which electrical energy from the electrodes passes (in operation, possibly including suture material, blood and saline). The power delivered through the electrodes should be sufficient to provided the desired welding effect, while not so much as to degrade the strength of the suture material being welded or to cause thermal damage to any nearby tissue. One such shut off mechanism includes a timer based on the power delivered through the electrodes. In this embodiment, a time-power relationship can be experimentally determined for a given suture material and, following actuation, energy source can time the power delivery and stop such delivery upon reaching a desired stop time. In one preferred embodiment, the desired stop time will be equal to or less than 5 seconds. Alternatively, a thermister or thermocouple could be located proximate to at least one electrode; power could then be shut off upon reaching a desired temperature. Still further, electrical impedance could be measured by the energy source for use as a metric in shutting off the power upon welding completion.

One preferred energy source 32 usable with the system of the invention is the VAPR® II Generator available from Mitek® Products of Westwood, Mass. This fully programmable energy source provides bipolar RF energy, and can include a variety of electrode types including those having a thermister located proximate to the electrode for monitoring temperature from the energy source.

Figure 2:
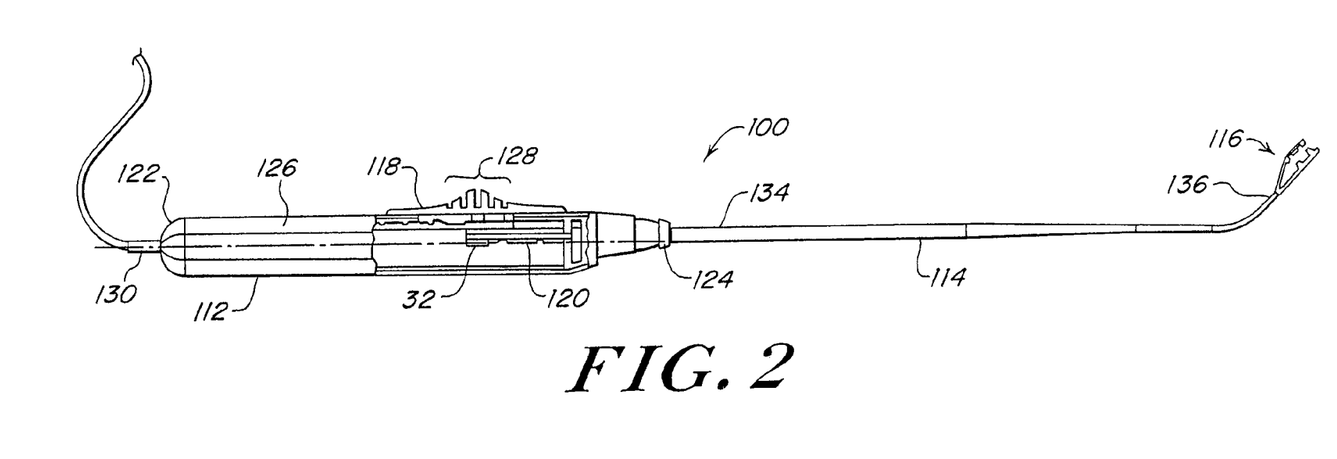
FIG. 2 is a side view, with a partial cut-away, of a suture welding device of the invention.
Figure 2A:
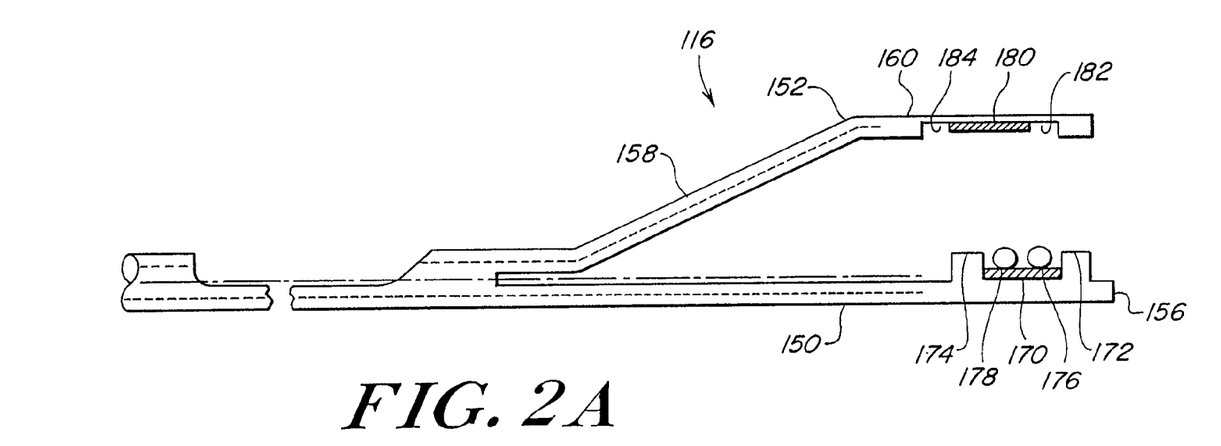
FIG. 2A is a side view of a suture grasper of the device of FIG. 2 in an open position with two lengths of suture.
Figure 2B:
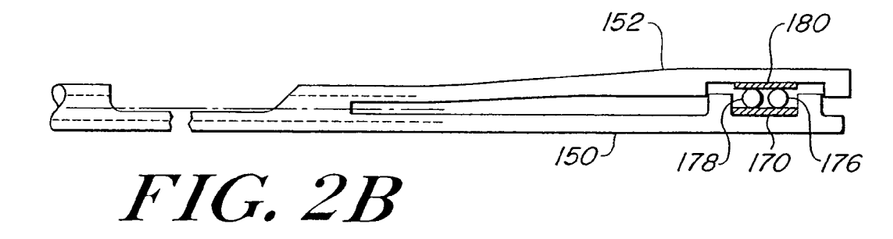
FIG. 2B is a side view of the suture grasper of FIG. 2A in an intermediate position.
Figure 2C:
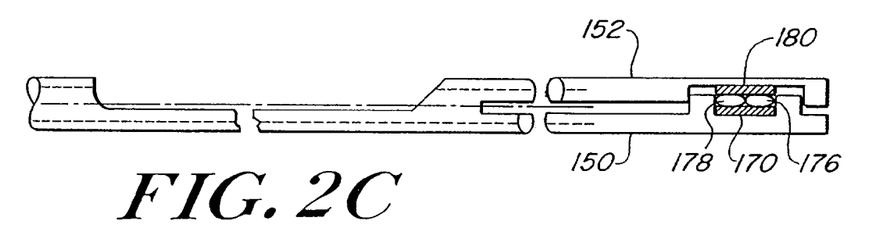
FIG. 2C is a side view of the suture grasper of FIG. 2A in a closed position.

FIGS. 2 through 2C illustrate an embodiment of a suture welding device 100 of the invention. As shown in FIG. 2, exemplary suture welding device 112 includes a handle or housing 112, a hollow extension tube 114, a suture grasper 116, an actuator 118 for operating the suture grasper, a linking member 120 which connects the actuator 118 to the suture grasper 116, and a longitudinal axis 130. The exemplary housing 112 is elongate, generally cylindrical and has opposed proximal 122 and distal 124 ends. The shape and dimensions of the housing may be selected by a person of ordinary skill in the art to allow the housing to be suitably grasped by a surgeon in an operating environment.

Actuator 118 is slidably mounted on a side wall 126 of housing 112. In this exemplary embodiment, the actuator has a rectangularly-shaped base and includes a series of flanges 128 having varying heights and angled surfaces so as to be easily manipulated in either of two directions by a surgeon's thumb. Actuator 118 is mounted so as to slide in a direction substantially parallel to a longitudinal axis 130 of housing 112. Actuator 118 is movable between a first position (shown in FIG. 2), wherein actuator 118 is closest to the distal end 124 of housing 112, and a second position (not illustrated), wherein actuator 118 is closest to the proximal end 122 of the housing. This movement of actuator 118, and corresponding movement of linking member 120, results in an interaction between suture grasper 116 and a distal end 136 of extension tube 114 that opens the suture grasper (see FIG. 2A) when the actuator is in the first position and closes the suture grasper (see FIG. 2C) when the actuator is in the second position. Actuator 118 may also be selectively positionable at locations between the first and second positions to result in a suture grasper 116 position that is between fully open and fully closed.

Suture welding device 100 is particularly suited to endoscopic, arthroscopic, or other minimally invasive uses as its configuration allows extension tube 114 to place suture grasper 116 within a patient proximate to a desired suture welding site while allowing handle or housing 112 to remain outside the patient where it can be readily manipulated by a surgeon. Illustrated extension tube 114 includes a bend of approximately 60° proximate to its distal end 136, however, extension tube 114 can be formed into a number of desirable geometries that might be suited to different specific procedures.

Exemplary suture grasper 116 has a first suture grasping member 150 and a second suture grasping member 152. First suture grasping member 150 is substantially straight and has an electrode 170 located near its distal end 156. Two extending pods 172, 174 are located adjacent to electrode 170 distally and proximally, respectively. Pods 172, 174 extend outward from suture grasping member 150 toward suture grasping member 152 so as to restrain lengths of suture 176, 178 that are in contact with electrode 170 from sliding off of the electrode in a proximal or distal direction.

Second suture grasping member 152 is shaped to include a first, angled segment 158 that angles away from the first suture grasping member 150, and a second segment 160 that extends from a distal end of first segment 158 and is closer to parallel with first suture grasping member 150. In further embodiments, second suture grasping member can include more than two segments and the segments may be angled differently in order to provide desired suture grasping effects. In addition, suture grasper 116 may include two suture grasping members that include angled segments rather than one as illustrated. In one embodiment, suture grasper 116 may include suture grasping members that are angled away from each other in equal amounts so that as actuator 118 is drawn distally, the suture grasping members approach being parallel with each other as they approach a closed position.

Second suture grasping member 152 can also include a second electrode 180 flanked distally and proximally by recesses 182, 184 that correspond in shape and location to pods 172, 174 on the first suture grasping member, respectively. Pods 172, 174 can interact with recesses 182, 184 as described below to maintain the position of lengths of suture 176, 178 with first and second electrodes 170, 180 when suture grasper 116 is placed in a closed position for welding.

The spaced-apart configuration of the first 150 and second 152 suture grasping members as shown in FIG. 2A is referred to herein as the "open" position. The flexible suture grasper 116 is biased to the open position and achieves that position when the suture grasper 116 is fully extended from the extension tube 114. The spacing between the suture grasping members 150, 152 can generally be in the range of about 0.020 to 0.250 inch, and is most preferably about 0.100 inch.

As actuator 118 is moved proximally from its distal-most position (where suture grasper 116 is in the open position), the angled first segment 158 of the second suture grasping member 152 contacts an inner wall of the distal end 136 of the hollow extension tube 114, and the second suture grasping member 152 is forced towards the first suture grasping member 150 as shown in FIG. 2B. As the actuator reaches an intermediate position, the pods 172, 174 of the first suture grasping member 150 interact with the recesses 182, 184 of the second suture grasping member to slidably restrain two lengths 176, 178 of suture thread within suture grasper 116. By using this intermediate position, a surgeon performing an endoscopic/arthroscopic procedure can place two ends of a suture thread to be welded within suture grasper 116 in its open state, move actuator 118 to an intermediate position, and slide the suture grasper down the suture threads to the desired welding site within the patient.

When actuator 118 is moved all of the way to its proximal-most position, suture grasper 116 is fully closed and two lengths of suture 176, 178 are tightly held within the grasper in close contact with electrodes 170, 180 as illustrated in FIG. 2C. Lengths of suture 176, 178 are illustrated in FIG. 2C as being deformed due to pressure applied to them by opposed electrodes 170, 180. Such deformation may or may not occur depending on the properties of the suture material and the amount of pressure applied, however, it is desirable that there be close physical contact between each electrode 170, 180 and each length of suture 176, 178. In this position, suture welding may be actuated by engaging foot pedal 36 (FIG. 1) or such other actuator as may be provided on energy source 32 or on suture welding device 100.

Electrodes 170, 180 are illustrated in an opposing configuration in FIGS. 1 through 2C, however, other configurations may be employed within the spirit of the invention. As discussed above, the electrode configuration could be monopolar, with only one electrode provided on suture welding device 12, 100. In addition, electrodes 170, 180 could be side by side rather than opposed.

In the illustrated configuration, electrodes 170, 180 are preferably long enough to allow two lengths of suture thread to be put into close contact with them. For typical use with monofilament suture sizes 0 to 20, suture diameter will be approximately 0.015 to 0.030 inch. Accordingly, an electrode length (measured in a left-right direction in FIGS. 2 to 2C) of less than or equal to approximately 0.060 inches will be sufficient to ensure that two lengths of such suture can be placed into contact with the electrodes. Electrode width (measured into or out of the page in FIGS. 2 to 2C) should be commensurate with the desired length of the weld created between lengths of suture thread 176, 178. For most typical uses, this width will be less than or equal to about 10 mm, and more likely less than or equal to about 7 mm. Electrodes 170, 180 can be formed from a variety of conductive metals, including conductive stainless steel, platinum, tungsten, platinum-iridium, and blends or alloys thereof. Of course, electrodes 170, 180 must be coupled to energy source 32 (FIG. 1) as may be accomplished by providing a conductive coupling from the electrodes to connector and cable 130 (FIG. 2) which in turn may be connected to the energy source.

Suture grasping members 150, 152 are preferably formed from a material that provides sufficient elasticity so as to be flexibly movably from the open position (illustrated in FIG. 2A) to the closed position (illustrated in FIG. 2C). More importantly, suture grasping members 150, 152 should be formed from a non-conducting material so as to resist the spurious flow of current from electrodes 170, 180 through the body of suture welding device 12, 100. Suture grasping members 150, 152 can also carry electrodes 170, 180 proximate to the distal end 156 of the members, and can also have a rounded distal end 156 to more easily permit the sliding of suture grasper 116 down the suture thread in restricted spaces or in close proximity to tissue, such as, for example, during and endoscopic or arthroscopic procedure in which tissue is being sutured and it is desirable to have the weld formed to snugly tie soft tissue for attachment purposes.

Lengths of suture 176, 178 can be formed from a material that will appropriately weld upon exposure to RF energy provided through electrodes 170, 180. Many plastics, including polymers, can be used, and, in particular, bioabsorbable and other plastics commonly used to make sutures can be used. Examples of particularly useful materials for forming sutures for use with the invention include prolene, and even more particularly, polydioxanone (PDS).

Figure 3:
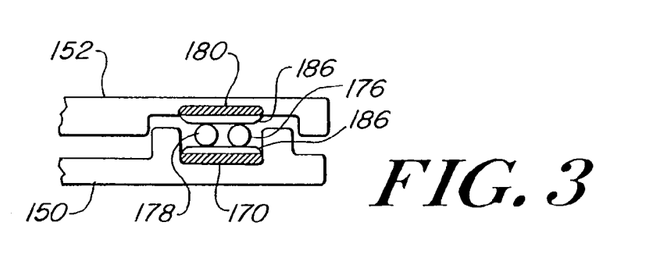
FIG. 3 is a side view of a portion of the suture grasper of FIG. 2A having weldable material supplied on electrodes thereon.
Figure 3A:
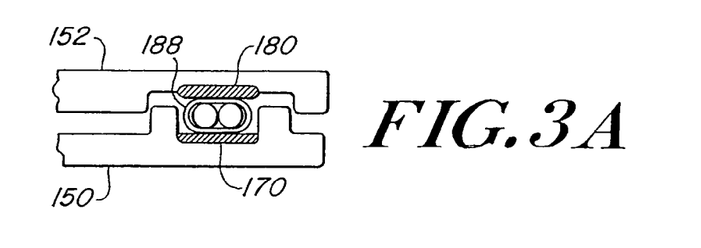
FIG. 3A is a side view of the suture grasper portion of FIG. 3 having weldable material provided in the form of a ring.

In addition to forming sutures from a weldable material, a separate ring or partial ring of weldable material could be provided in conjunction with the suture or with the suture welding device as illustrated in FIGS. 3 and 3A. As shown in FIG. 3, a suture grasper 116 is provided having electrodes 170, 180 where each electrode has a weldable material 186 preformed thereon. Upon heating, weldable material 186 preferably wicks onto sutures 176, 178 and melts around them to bond them together. Weldable material 186 may include a release layer formed adjacent to the electrodes to aid in the flow of the weldable material to the sutures. A further embodiment is illustrated in FIG. 3A in which weldable material 188 is formed as a ring or collar around sutures 176, 178. Upon heating by electrodes 170, 180, weldable material 188 melts around lengths of suture 176, 178 and thereby fixes the lengths of suture to each other.

Figure 4:
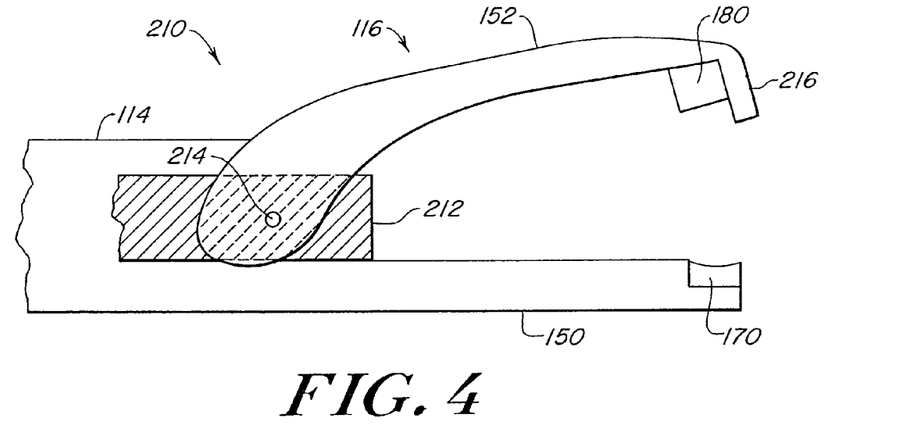
FIG. 4 is a side view, with a partial cut-away, of an alternative suture grasper in an open position.
Figure 4A:
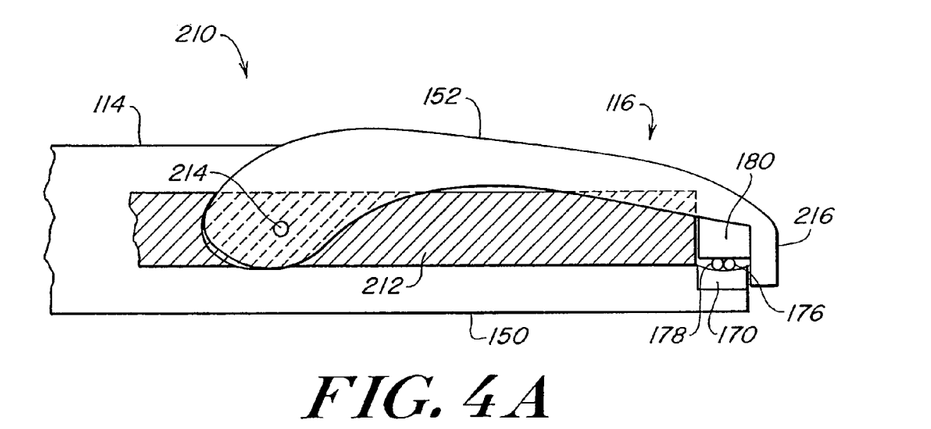
FIG. 4A is a side view, with a partial cut-away, of the suture grasper of FIG. 4 in a closed position.

A further embodiment of a suture welding device 210 of the invention having a rotating suture grasping member 152 and a slidable piston 212 is illustrated in FIGS. 4 and 4A. As with suture welding device 100, Suture welding device 210 includes a hollow extension tube 114 and a suture grasper 116. Suture grasper 116 has a first suture grasping member 150 and a second suture grasping member 152, each of which has a distally located electrode 170, 180, respectively. In this embodiment, second suture grasping member 152 is linked to extension tube 114 by one or more hinges 214 which allow suture grasping member 152 to rotate between open (illustrated in FIG. 4 with spaced apart suture grasping members) and closed (illustrated in FIG. 4A positions) in response to an actuator (not shown). Piston 212 is slidable in a proximal-distal direction and can be used to push lengths of suture 176, 178 into contact with electrodes 170, 180 by activation of the same or a different actuator as used to operate suture grasping member 152.

Like suture welding device 100, suture welding device 210 preferably includes an intermediate position wherein lengths of suture 176, 178 are slidably retained within suture grasper 116 so that electrodes 170, 180 can slide down the suture material to the desired welding site before suture grasper 116 is closed and welding is initiated. Rather than using the extending pods and corresponding recesses provided on the suture grasper to hold lengths of suture as illustrated on suture welding device 100 (FIGS. 2 to 2C), suture welding device 210 includes a single extending pod 216 at a distal end of one of the two suture grasping members 150, 152. Pod 216 can overlap with an opposed suture grasping element (illustrated in FIG. 4A with pod 216 overlapping with suture grasping member 150) to prevent lengths of suture thread 176, 178 from escaping suture grasper 116 distally. This overlap can occur before full closing of suture grasper 116 in order to slidably retain the sutures within the grasper in an intermediate position.

In the illustrated embodiment, electrodes 170, 180 are disposed in an opposed relationship on suture grasping members 150, 152, respectively, however, a person of ordinary skill in the art will recognize that other electrode configurations can be employed within the spirit of the invention. For example, electrodes 170, 180 could be placed in opposition on a distal facing end of piston 212 and a proximal facing face of pod 216, or electrodes 170, 180 could be placed in a side by side relationship on either of those two faces, or on suture grasping member 150, or on suture grasping member 152. Also, electrode 170 can be provided with a surface curved in a concave manner so that when lengths of suture 176, 178 are pressed into contact with electrode 170, they will also be urged into contact with each other as illustrated in FIG. 4A.

Figure 5:
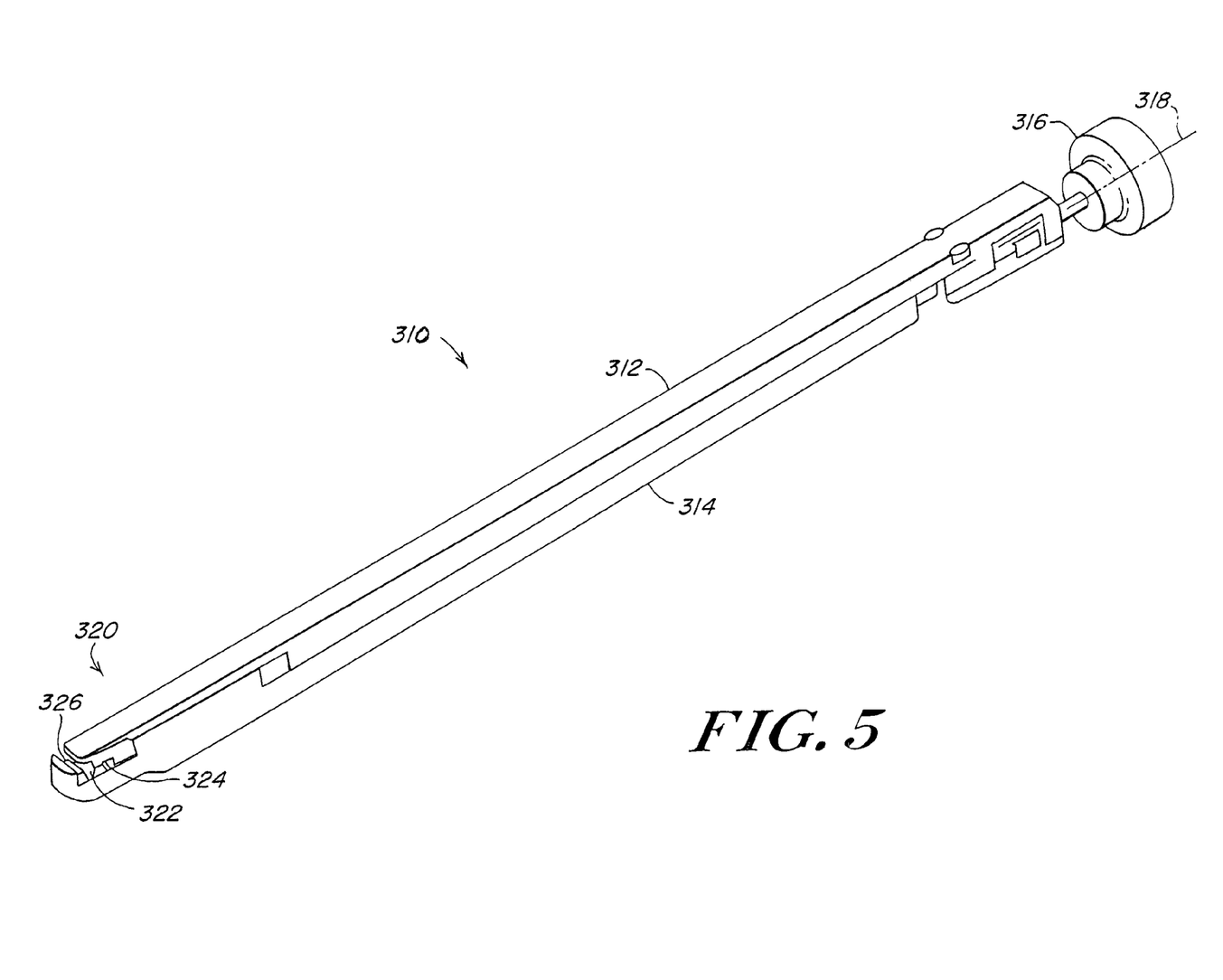
FIG. 5 is a perspective view of an alternative suture welding device of the invention.

A further suture welding device 310 of the invention is illustrated in FIG. 5. Suture welding device 310 includes a suture grasper 320 having a first, stationary suture grasping member 312 and a second, longitudinally translatable suture grasping member 314. Rotation of rotary actuator 316 causes second suture grasping member 314 to translate in a longitudinal direction (along a longitudinal axis 318 defined by suture welding device 310) with respect to first suture grasping member 312. Suture welding device 310 is illustrated in the open position, and it can be closed by rotating rotary actuator 316 so as to close gap 322 to capture any lengths of suture (none shown) located therein. First and second suture grasping members 312, 314 carry first and second electrodes 324, 326, respectively. Accordingly, closing gap 322 by rotating rotary actuator 316 effectively traps lengths of suture (not shown) between electrodes 324, 326 for welding. As with the other suture welding device embodiments, additional electrode shapes and configurations may be employed.

A person of ordinary skill in the art will appreciate further features and advantages of the invention based on the above-described embodiments. Accordingly, the invention is not to be limited by what has been particularly shown and described, except as indicated by the appended claims. All publication and references cited herein are expressly incorporated herein by reference in their entirety.

What is claimed is:

1. A suture welding system for fixedly attaching a first length of suture to a second length of suture at a suture welding site, comprising:
   an electrosurgical energy source configured to generate radio frequency waves;
   first and second lengths of suture; and
   a suture welding device, having:
      a working end;
      a suture contacting element located on the working end and having the first and second lengths of suture disposed thereon;
      a first electrode electrically coupled to the electrosurgical energy source and disposed on the suture contacting element for providing radio frequency energy to the first and second lengths of suture; and
      a second electrode electrically coupled to the electrosurgical energy source and disposable proximate to the suture welding site for providing a return electrical energy path to the electrosurgical energy source;

wherein provision of radio frequency energy by the first electrode to the first and second lengths of suture welds the first and second lengths of suture into a fixed attachment.

2. The system according to claim 1 wherein the suture contacting element comprises two opposing faces having a variable gap therebetween, each face having one of the first electrode or the second electrode disposed thereon.

3. The system according to claim 2 wherein the suture welding device is configured to be selectively adjustable between an open position and a closed position, wherein the first and second lengths of suture may be placed within the variable gap in the open position and wherein the lengths of suture are constrained within the variable gap in the closed position.

4. The system of claim 3 wherein the suture contacting element is configured to force the first and second length of suture into close physical contact when the suture welding device is placed in the closed position.

5. The system according to claim 1 wherein the first and second lengths of suture are made of material selected from the group consisting of polydioxanone, prolene, and polymer plastics.

6. The system according to claim 1 wherein the first and second lengths of suture are made of polydioxanone.

7. The system according to claim 1 wherein a weldable material is provided between at least one electrode and at least one length of suture, the weldable material adapted to weld the first length of suture thread to the second length of suture thread upon application of radio frequency energy through the at least one electrode.

8. The suture welding device of claim 1,
wherein the suture welding device includes a piston slidingly disposed on the suture welding device so as to be translatable in a longitudinal direction to move the first and second lengths of suture into contact with at least one electrode.

9. The system of claim 1 wherein the suture contacting element has at least one pod configured to prevent the first and second sutures from sliding off of the suture contacting element.

10. A method for welding a first length of suture to a second length of suture to create a fixed attachment therebetween, comprising:
(a) providing an electrosurgical energy source;
(b) providing a suture welding device, having:
a working end;
a suture contacting element disposed on the working end, the suture contacting element having two opposing faces having a variable gap therebetween, each face having one of a first electrode and a second electrode disposed thereon;
the first electrode electrically coupled to the electrosurgical energy source and disposed on the suture contacting element for providing electrical energy to the first and second lengths of suture; and
the second electrode electrically coupled to the electrosurgical energy source and disposable proximate to the suture welding site for providing a return electrical energy path to the electrosurgical energy source;
(c) placing a first length of suture and a second length of suture into contact with the suture contacting element; and (d) providing energy from the electrosurgical energy source through the first electrode to the first and second lengths of suture to weld the first length of suture to the second length of suture to create a fixed attachment therebetween.

11. The method of claim 10 wherein the electrosurgical energy source generates radio frequency waves.

12. The method of claim 11 wherein the suture welding device is configured to be selectively adjustable between an open position and a closed position, wherein the first and second lengths of suture may be placed within the variable gap in the open position and wherein the lengths of suture are constrained within the variable gap in the closed position.

13. The method of claim 12 wherein the suture contacting element forces the first and second lengths of suture into close physical contact with each other when the suture welding device is placed in the closed position.

14. The method of claim 10 wherein the suture contacting element has at least one pod configured to prevent the first and second sutures from sliding off of the suture contacting element.

15. The method of claim 10 wherein the first and second lengths of suture are made from polydioxanone.

16. A suture welding system for fixedly attaching a first length of suture to a second length of suture at a suture welding site, comprising:
an electrosurgical energy source; and
a suture welding device, having:
a working end;
a suture contacting element disposed on the working end, the suture contacting element having at least one pod configured to prevent the first and second sutures from sliding off of the suture contacting element;
a first electrode electrically coupled to the electrosurgical energy source and disposed on the suture contacting element for providing electrical energy to the first and second lengths of suture; and
a second electrode electrically coupled to the electrosurgical energy source and disposable proximate to the suture welding site for providing a return electrical energy path to the electrosurgical energy source;
wherein provision of electrical energy by the first electrode to the first and second lengths of suture welds the first and second lengths of suture into a fixed attachment.

17. The system of claim 16 wherein the electrosurgical energy source generates radio frequency waves.

18. The system of claim 16 wherein the suture contacting element comprises two opposing faces having a variable gap therebetween, each face having one of the first electrode or the second electrode disposed thereon.

19. The system of claim 18 wherein the suture welding device is configured to be selectively adjustable between an open position and a closed position, wherein the first and second lengths of suture may be placed within the variable gap in the open position and wherein the lengths of suture are constrained within the variable gap in the closed position.

20. The system of claim 19 wherein the suture contacting element is configured to force the first and second length of suture into close physical contact when the suture welding device is placed in the closed position.

21. The system of claim 16, wherein the first and second lengths of suture are made of polydioxanone.

* * * * *